(12) United States Patent
Reiderman

(10) Patent No.: US 7,663,363 B2
(45) Date of Patent: Feb. 16, 2010

(54) METHOD AND APPARATUS FOR HIGH SIGNAL-TO-NOISE RATIO NMR WELL LOGGING

(75) Inventor: Arcady Reiderman, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 286 days.

(21) Appl. No.: 11/756,863

(22) Filed: Jun. 1, 2007

(65) Prior Publication Data

US 2007/0222444 A1 Sep. 27, 2007

Related U.S. Application Data

(63) Continuation-in-part of application No. 11/494,043, filed on Jul. 27, 2006, which is a continuation-in-part of application No. 11/037,488, filed on Jan. 18, 2005.

(60) Provisional application No. 60/542,932, filed on Feb. 9, 2004.

(51) Int. Cl.
*G01V 3/00* (2006.01)
*G01R 33/20* (2006.01)

(52) U.S. Cl. .................. 324/303; 324/306; 324/314

(58) Field of Classification Search .......... 324/300–322; 600/407–435
See application file for complete search history.

(56) References Cited

U.S. PATENT DOCUMENTS

| | | | |
|---|---|---|---|
| 3,049,662 A * | 8/1962 | Ionel et al. ............... | 324/301 |
| 3,238,446 A * | 3/1966 | Zimmerman ............ | 324/303 |
| 3,538,429 A | 11/1970 | Baker, Jr. | |
| 3,597,681 A | 8/1971 | Huckabay | |
| 3,731,752 A | 5/1973 | Schad | |
| 4,035,718 A | 7/1977 | Chandler | |
| 4,489,276 A | 12/1984 | Yu | |
| 4,536,714 A | 8/1985 | Clark | |
| 4,538,109 A | 8/1985 | Clark | |
| 4,574,242 A | 3/1986 | Clark et al. | |
| 4,584,586 A | 4/1986 | Kocsi | |
| 4,603,297 A | 7/1986 | Safinya | |
| 4,717,878 A | 1/1988 | Taicher et al. | |
| RE32,913 E | 4/1989 | Clark | |

(Continued)

FOREIGN PATENT DOCUMENTS

WO 02056047 A1 7/2002

OTHER PUBLICATIONS

U.S. Appl. No. 11/743,863. "Selective Excitation in Earth's Magnetic Field Nuclear Magnetic Resonance Well Logging Tool". Filed May 3, 2007. 33 pages.

(Continued)

*Primary Examiner*—Brij B. Shrivastav
*Assistant Examiner*—Tiffany A Fetzner
(74) *Attorney, Agent, or Firm*—Cantor Colburn LLP

(57) ABSTRACT

A method for measuring nuclear magnetic properties (NMR) properties of a formation, the method including applying a magnetic field to nuclei of the formation during a polarizing interval, the magnetic field having a polarizing intensity; changing the magnetic field to a measurement intensity, the measurement intensity applied to the nuclei of the formation during a measurement interval; applying to the formation at least one radio frequency (RF) pulse train during the measurement interval; and measuring an NMR signal from the formation.

19 Claims, 12 Drawing Sheets

U.S. PATENT DOCUMENTS

| | | | |
|---|---|---|---|
| 5,055,787 A | 10/1991 | Kleinberg et al. | |
| 5,600,330 A | 2/1997 | Blood | |
| 5,710,511 A | 1/1998 | Taicher et al. | |
| 5,955,884 A | 9/1999 | Payton et al. | |
| 6,002,317 A | 12/1999 | Pignataro | |
| 6,166,543 A | 12/2000 | Sezginer et al. | |
| 6,229,422 B1 | 5/2001 | Pignataro | |
| 6,348,792 B1 | 2/2002 | Beard et al. | |
| 6,366,086 B1 | 4/2002 | Sen | |
| 6,452,388 B1 | 9/2002 | Reiderman et al. | |
| 6,459,262 B1 * | 10/2002 | Wisler et al. | 324/303 |
| 6,541,979 B2 | 4/2003 | Omeragic | |
| 6,556,015 B1 | 4/2003 | Omeragic et al. | |
| 6,580,273 B2 | 6/2003 | Reiderman et al. | |
| 6,584,408 B2 | 6/2003 | Omeragic | |
| 6,690,170 B2 | 2/2004 | Homan et al. | |
| 6,703,833 B2 * | 3/2004 | Wisler et al. | 324/303 |
| 6,727,705 B2 | 4/2004 | Frey et al. | |
| 6,819,110 B2 | 11/2004 | Omeragic et al. | |
| 6,819,112 B2 | 11/2004 | Gianzero et al. | |
| 6,891,376 B2 | 5/2005 | Hanstein et al. | |
| 6,930,652 B2 | 8/2005 | Smith et al. | |
| 6,933,726 B2 | 8/2005 | Chen et al. | |
| 6,937,021 B2 | 8/2005 | Rosthal | |
| 7,023,212 B2 | 4/2006 | Chen et al. | |
| 7,138,897 B2 | 11/2006 | Ninerbo et al. | |
| 7,193,420 B2 | 3/2007 | Chen et al. | |
| 7,202,670 B2 | 4/2007 | Omeragic et al. | |
| 2002/0175681 A1 * | 11/2002 | Taicher | 324/303 |
| 2002/0196018 A1 * | 12/2002 | Wisler et al. | 324/303 |
| 2004/0183538 A1 | 9/2004 | Hanstein et al. | |
| 2004/0263414 A1 | 12/2004 | Chen et al. | |
| 2005/0116718 A1 | 6/2005 | Chen et al. | |
| 2005/0140373 A1 | 6/2005 | Li et al. | |
| 2005/0189945 A1 | 9/2005 | Reiderman | |
| 2006/0192561 A1 | 8/2006 | Chesser et al. | |
| 2006/0192562 A1 | 8/2006 | Davydychev et al. | |
| 2006/0253255 A1 | 11/2006 | Omeragic et al. | |
| 2006/0255799 A1 | 11/2006 | Reiderman | |
| 2007/0222444 A1 * | 9/2007 | Reiderman | 324/303 |

OTHER PUBLICATIONS

International Search Report for International Application No. PCT/US2008/065265. Mailed Aug. 12, 2008.

Written Opinion of the International Searching Authority for International Application No. PCT/US2008/065265. Mailed Aug. 12, 2008.

* cited by examiner

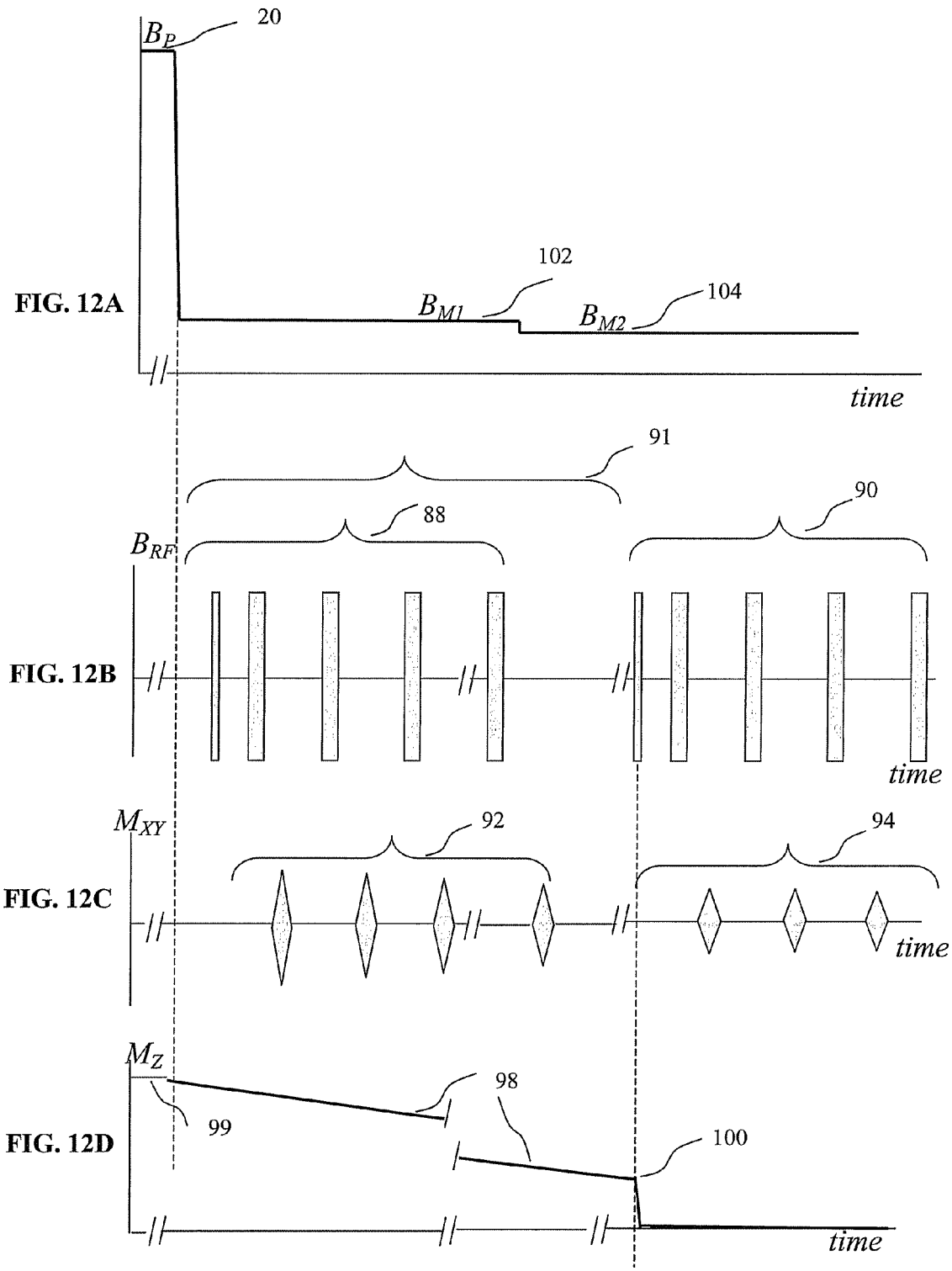

METHOD AND APPARATUS FOR HIGH SIGNAL-TO-NOISE RATIO NMR WELL LOGGING

CROSS-REFERENCES TO RELATED APPLICATIONS

This application is filed under 37 CFR 1.53(b) as a continuation-in-part of and claims priority under 35 U.S.C. 120 to U.S. patent application Ser. No. 11/494,043 filed on Jul. 27, 2006, which in turn claims priority to U.S. patent application Ser. No. 11/037,488 filed on Jan. 18, 2005, which in turn claims priority to U.S. Provisional Patent Application No. 60/542,932 filed on Feb. 9, 2004, these applications being incorporated by reference in their entirety.

BACKGROUND OF THE INVENTION

1. Field of the Invention

The present invention relates to using nuclear magnetic resonance to measure properties of an earth formation. Specifically, the measuring is performed in a borehole.

2. Description of the Related Art

In exploration for hydrocarbons, it is important to make accurate measurements of geologic formations. The geologic formations below the surface of the earth may contain reservoirs of oil and gas. The geologic formations may include formation layers and various structures. In a quest for oil and gas, it is important to know about the location and composition of the formation bedding planes and the various structures. In particular, it is important to know about the geologic formations with a high degree of accuracy so that resources are not wasted. Measuring properties of the geologic formations provides information that can be useful for locating the reservoirs of oil and gas. Typically, the oil and gas are retrieved by drilling boreholes into the subsurface of the earth. The boreholes also provide access for taking measurements of the geologic formations.

Well logging is a technique used to take measurements of the geologic formations from the boreholes. In one embodiment, a "logging instrument" is lowered on the end of a wireline into the borehole. The logging tool sends data via the wireline to the surface for recording. Output from the logging instrument comes in various forms and may be referred to as a "log." One type of measurement involves using nuclear magnetic resonance (NMR) to measure properties of the geologic formations.

A recent generation of nuclear magnetic resonance (NMR) logging instruments based on using permanent magnets was introduced about a decade ago (see, for example, U.S. Pat. No. 4,717,878 issued to Taicher et al., U.S. Pat. No. 5,055,787 issued to Kleiberg et al., and U.S. Pat. No. 6,452,388 issued to Reiderman et al.). The recent generation of NMR logging instruments demonstrated advantages over previous NMR technologies such as earth's magnetic field NMR logging. Advantages provided included higher signal-to-noise-ratio (SNR), higher resolution in acquiring NMR relaxation spectra, capability of diffusion measurements, and a defined volume of investigation with no effects of protons in a borehole fluid on acquired NMR data.

The recent generation of NMR logging instruments typically exhibited a high rate of decreasing a static magnetic field of the permanent magnet with distance from an NMR sensor. The high rate of decreasing the static magnetic field generally results in a relatively small region of investigation. As a consequence of the small region of investigation, the SNR of NMR measurements is too low to allow for a desired logging speed with acceptable vertical resolution. The low SNR also limits the NMR measurements to a depth of investigation of about two to four inches. The depth of investigation of about two to four inches is a region substantially invaded by drill mud spurt. In general, the drill mud spurt interferes with talking accurate NMR measurements of the geologic formations.

What are needed are apparatus and methods for performing the NMR measurements with a higher SNR than previously achieved in a logging instrument. Preferably, the higher SNR allows for the desired logging speed with acceptable vertical resolution and for the region of investigation exceeding two to four inches of depth.

BRIEF SUMMARY OF THE INVENTION

The shortcomings of the prior art are overcome and additional advantages are provided through a method for measuring nuclear magnetic resonance (NMR) properties of a formation, the method including applying a magnetic field to nuclei of the formation during a polarizing interval, the magnetic field having a polarizing intensity; changing the magnetic field to a measurement intensity, the measurement intensity applied to the nuclei of the formation during a measurement interval; applying to the formation at least one radio frequency (RF) pulse train during the measurement interval; and measuring an NMR signal from the formation.

Also disclosed is an instrument for measuring nuclear magnetic resonance (NMR) properties of a formation from a borehole, the instrument including a magnetic core; at least one switching winding disposed about the magnetic core, wherein the winding conducts electrical current to magnetize the core and is adapted to switch between a polarizing magnetic field and a measurement magnetic field; and an antenna for at least one of transmitting a radio frequency (RF) pulse train and receiving a NMR signal.

Also disclosed is a computer program product stored on machine-readable media, the product including instructions for measuring nuclear magnetic resonance (NMR) properties of a formation from a borehole, the instructions including instructions for applying a magnetic field to nuclei of the formation during a polarizing interval, the magnetic field comprising a first polarizing intensity; decreasing the magnetic field to a first measurement intensity, the first measurement intensity applied to the nuclei of the formation during a measurement interval; applying to the formation at least one radio frequency (RF) pulse train during the measurement interval; and measuring an NMR signal from the formation.

Further disclosed is a method for producing a logging instrument for measuring nuclear magnetic resonance (NMR) properties of a formation from a borehole, the method including selecting a magnetic core; placing at least one switching winding about the magnetic core, wherein the winding conducts electrical current to magnetize the core and is adapted to switch between a polarizing magnetic field and a measurement magnetic field; selecting an antenna; and placing the magnetic core, the winding; and the antenna into an assembly, wherein the logging instrument includes the assembly.

BRIEF DESCRIPTION OF THE DRAWINGS

Referring now to the drawings wherein like elements are numbered alike in the several Figures:

FIGS. 12A, 12B, 12C, and 12D, collectively referred to as FIG. 12, illustrate exemplary graphs of the static magnetic field with two intensities, two CPMG trains, and magnetization versus time;

DETAILED DESCRIPTION OF THE INVENTION

Figure 1:
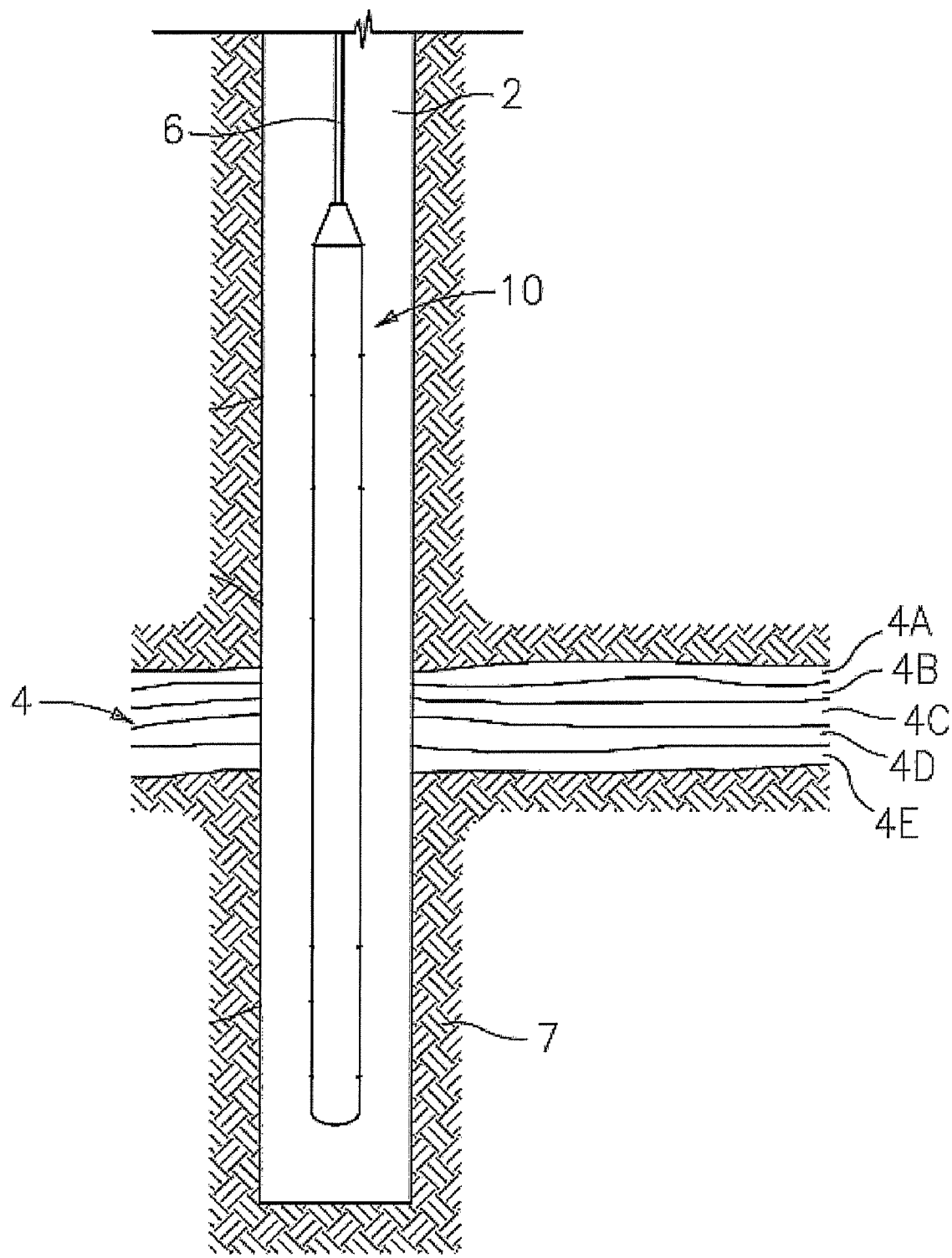
FIG. 1 illustrates an exemplary embodiment of a logging instrument in a borehole penetrating the earth.

The teachings provide apparatus and methods for performing nuclear magnetic resonance (NMR) measurements with a high signal-to-noise ratio (SNR). The high SNR provides for a logging speed of about thirty to forty feet per minute with a vertical resolution of measurement of about two to four feet. The high SNR also provides for performing NMR measurements of geologic formations beyond regions invaded with drill mud spurt.

In typical embodiments, the apparatus includes an elongated switchable magnet and sensing coil with a high number of turns for use in a well logging instrument. Also in typical embodiments, the method calls for applying to nuclei in a region of investigation a high polarizing magnetic field then a relatively lower measurement magnetic field. While the measurement magnetic field is being applied, a series of radio frequency pulses at a low frequency is also applied to the nuclei. Echoes resulting from precession of the nuclei are measured to determine characteristics of the region of investigation. The low frequency of the radio frequency pulses allows for an increased number of turns in a receiving coil receiving the echoes. It follows that the increased number of turns provides for the high SNR. Before the apparatus and the method are discussed in detail certain definitions are provided.

As a matter of convention, one should note that the variables used herein appear throughout the disclosure. Accordingly, previously defined variables are generally not reintroduced. For convenience of referencing, the following definitions are provided. The term "$M_z(t)$" represents a longitudinal magnetization, which involves a time constant $T_1$, where $T_1$ is the time required for the magnetization vector to be restored to 63% of its original amplitude (referred to as "longitudinal relaxation time"). The term "$M_{xy}(t)$" represents a transverse magnetization, which involves a time constant $T_2$, where $T_2$ is the time required for the magnetization vector to drop to 37% of its original amplitude (referred to as "transverse relaxation time"). The term "radio frequency (RF) pulse train" with respect to NMR measurements relates to a series of radio frequency pulses designed to produce NMR signals from the geologic formations. Typically, the RF pulse train is a CPMG pulse train that includes an "initial pulse" also referred to as a "preparatory pulse." The initial pulse is applied to rotate nuclear spins into a plane perpendicular to a static magnetic field. As the nuclei precess in the static magnetic field, the nuclei produce the NMR signal (called free induction decay). The nuclei eventually dephase and stop producing the NMR signal. Another radio frequency pulse following the initial pulse re-aligns the nuclei in the perpendicular plane to produce a spin-echo. Successive radio frequency pulses, referred to as "refocusing pulses," are used to re-magnetize the nuclei after the nuclei spins dephase. In some embodiments, the RF pulse train may include one RF pulse. The term "excitation" relates to applying the static magnetic field and the CPMG pulse train to the nuclei of the geologic formation. The excitation causes the nuclei to precess and produce the spin-echoes. The spin-echoes are also referred to as "NMR echo signals and "NMR signals."

Referring to FIG. 1, a well logging instrument 10 is shown disposed in a borehole 2. The borehole 2 is drilled through earth 7 and penetrates formation 4, which include various layers 4A-4E. The instrument 10 is typically lowered into and withdrawn from the borehole 2 by use of an armored electrical cable 6 or similar conveyance as is known in the art. As used herein, the well logging instrument 10 is used for taking nuclear magnetic resonance measurements with high SNR of the formations 4.

In typical embodiments, the borehole 2 includes materials such as would be found in oil exploration, including a mixture of liquids including water, drilling fluid, mud, oil and formation fluids that are indigenous to the various formations. One skilled in the art will recognize that the various features as may be encountered in a subsurface environment may be referred to as "formations." Accordingly, it should be considered that while the term "formation" generally refers to geologic formations of interest, that the term "formations," as used herein, may, in some instances, include any geologic points of interest (such as a survey area).

Figure 2:
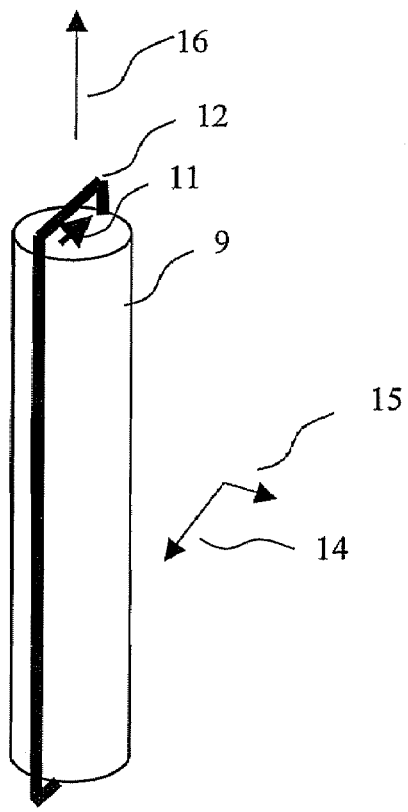
FIG. 2 illustrates an exemplary embodiment of a prior art magnet used for NMR well logging measurements.
Figure 3:
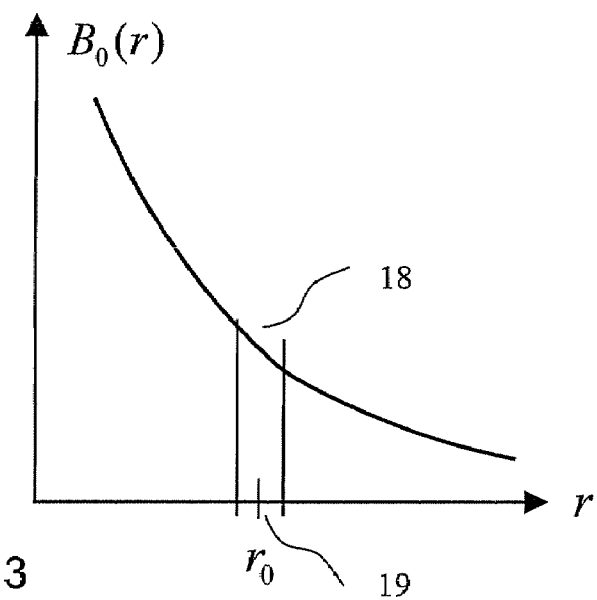
FIG. 3 illustrates a prior art example of radial dependency of a magnetic field.

FIG. 2 represents an exemplary embodiment of a sensor unit of a NMR well logging measurement of prior art. Referring to FIG. 2, a permanent magnet 9 is transversally magnetized in direction 11. The permanent magnet 9 generates a static magnetic filed $B_0$ that decays radially (with radius r) from the permanent magnet 9 as $B_0 \propto 1/r^2$. FIG. 3 illustrates a prior art radial dependency of the static magnetic field $B_0$. The static magnetic field $B_0$ exhibits a gradient for a range of r. Referring to FIG. 2, a radio frequency (RF) magnetic field $B_{RF}$ that is typically pulsed, is generated by an antenna 12. The static magnetic field $B_0$ has a direction 14. The RF magnetic field $B_{RF}$ has a direction 15. The static magnetic field $B_0$ and the RF magnetic field $B_{RF}$ are mutually orthogonal. Typically, the NMR measurements are performed while the logging instrument 10 is moving in an axial direction 16 (direction of axis of the borehole 2). To facilitate a substantial translational symmetry required for performing the NMR measurements while the logging instrument 10 is moving, the permanent magnet 10 and the antenna 12 are made elongated. Elongation also ensures a substantial axial symmetry of magnitudes of the static magnetic field $B_0$ and the RF magnetic field $B_{RF}$. Due to the gradient of the static magnetic field $B_0$ in the radial direction, nuclei are excited only in substantially a narrow excitation region where the static magnetic field $B_0$ corresponds to a frequency of the RF magnetic field $B_{RF}$. The frequency lies within a frequency band $\Delta\omega$ that is included within a bandwidth of the RF magnetic field $B_{RF}$. An example of a narrow excitation region 19 about $r=r_0$ corresponding to an operating frequency $\omega_0$ of the RF magnetic field $B_{RF}$ is shown in FIG. 3. FIG. 3 also illustrates a gradient 18 associated with the excitation region 19. A thickness $\Delta r$ of an excitation "shell" is given by $$\Delta r = \frac{\Delta\omega}{\gamma \cdot G_0}, \tag{1}$$

where $\gamma$ is the gyro-magnetic ratio for the nuclei, and $G_0$ is the gradient of the static magnetic field $B_0$ at $r=r_0$.

Based on the Reciprocity Principle, an NMR signal (S) induced in the antenna 12 can be calculated as follows:

$$S \approx \omega_0 \cdot M_n \cdot B'_A \cdot V_s \tag{2}$$

where $\omega_0$ is the operating frequency; $M_n$ is magnetization of the nuclei; $B'_A$ is an antenna sensitivity function for the antenna 12 (i.e., the RF magnetic field $B_{RF}$ produced by unit current flowing in the antenna 12); and $V_s$ is a sensitive volume.

The following equations can be written for the operating frequency $\omega_0$ and the sensitive volume $V_S$.

$$\omega_0 = \gamma \cdot B_0 \tag{3}$$

$$V_s = \frac{\Delta\omega}{\gamma \cdot G_0} \cdot 2\pi \cdot r_0 \cdot l_A \tag{4}$$

(where $l_A$ is the length of the antenna 12)

For $B_0 \propto 1/r^2$, the gradient of the static magnetic field $B_0$ at $r=r_0$ can be expressed as follows.

$$G_0 = \frac{2 \cdot B_0}{r_0} \tag{5}$$

Because the operating frequency $\omega_0$ (from equation (3)) is proportional to the static magnetic field $B_0$ and the sensitive volume (from equations (4) and (5)) is inversely proportional to the static magnetic field $B_0$, the NMR signal (from equation (2)) does not depend on the static magnetic field $B_0$. Substituting equations (5), (4), and (3) into equation (2), the NMR signal may be written as follows.

$$S \approx \pi \cdot M_n \cdot B'_A \cdot \Delta\omega \cdot r_0^2 \cdot l_A. \tag{6}$$

Referring to equation (6), it can be noted that lowering the operating frequency $\omega_0$ will not result in a lower NMR signal S. It can also be noted that a lower operating frequency $\omega_0$ will result from a lower static magnetic field $B_0$ in accordance with equation (3) and that the lower $B_0$ corresponds to a smaller static magnetic field gradient $G_0$ in accordance with equation (5). Referring to equation (1), it can be seen that the smaller static magnetic field gradient $G_0$ will result in a larger $\Delta r$. The larger $\Delta r$ (or larger radial extent of the sensitive volume) provides for better stability of the NMR measurements with respect to transversal motion of the logging instrument 10.

The prior art magnet (the permanent magnet 10) presented in FIG. 2 provides the static magnetic field $B_0$ that serves as a polarizing magnetic field and a measurement magnetic field. Typically, the magnetization $M_n$ is proportional to the static magnetic field $B_0$ polarizing the nuclei. Therefore, with respect to equation (6), the NMR signal S has a linear dependence on the static magnetic field $B_0$. In cases using the permanent magnet 10, lowering the operating frequency $\omega_0$ for a given radius of investigation $r_0$ results in reducing the static magnetic field $B_0$ and correspondingly the magnetization $M_n$. Thus, lowering the operating frequency $\omega_0$ results in lowering the NMR signal S in prior art NMR systems.

Figure 4A:
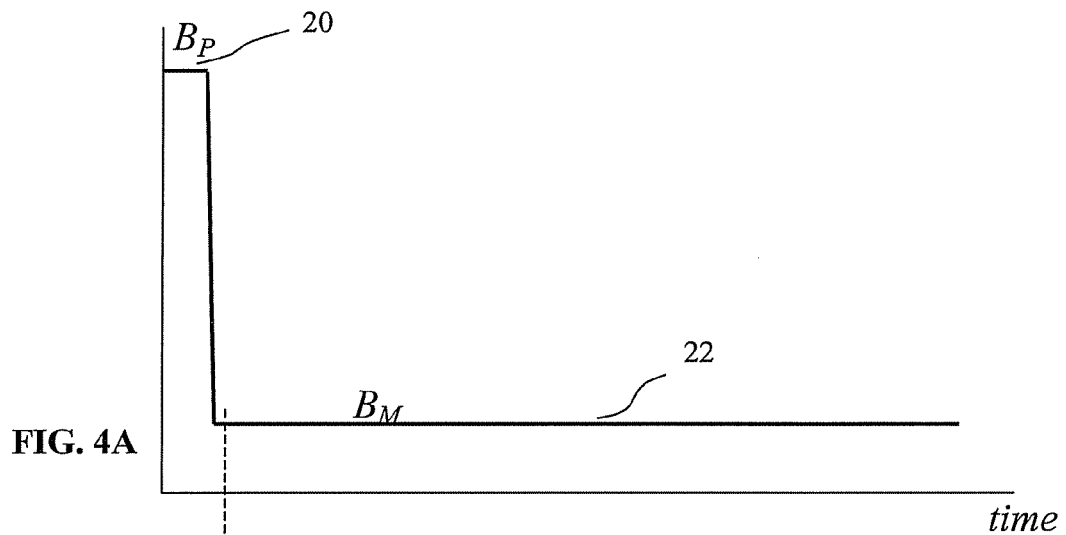
FIGS. 4A, 4B, 4C, and 4D, collectively referred to as FIG. 4, depict exemplary aspects of magnetic fields and resulting magnetization used in the NMR well logging measurements.
Figure 4B:
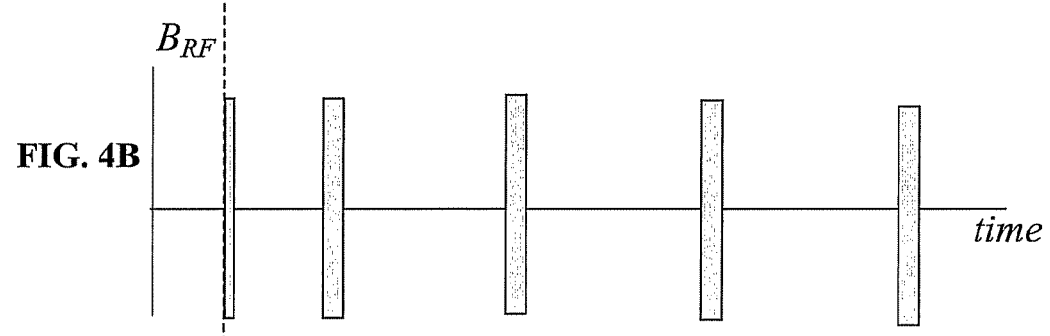

The teachings provide different static magnetic field intensities during polarization and measurement time intervals. The different static magnetic field intensities are referred to as a polarizing magnetic field $B_P$ (the static magnetic field with intensity $B_P$ and the measurement magnetic field $B_M$ (the static magnetic field with intensity $B_M$). The polarizing magnetic field $B_P$ and the measurement magnetic field $B_M$ are provided by a magnet that is "switchable." FIG. 4 depicts exemplary aspects of magnetic fields and resulting magnetization used in NMR measurements with the different static magnetic field intensities. Referring to FIG. 4, the nuclei are polarized by a polarizing magnetic field $B_P$ 20. Typically, the polarizing magnetic field $B_P$ 20 has a high magnitude. The polarizing magnetic field $B_P$ 20 is generally applied for a period of time comparable with a maximum expected longitudinal relaxation time. After the polarizing magnetic field $B_P$ 20 is applied, the polarizing magnetic field $B_P$ 20 is reduced by a factor of three to ten to produce a measurement magnetic field $B_M$ 22. The measurement magnetic field $B_M$ 22 is used for NMR relaxation measurements. The time interval for switching from the polarizing magnetic field $B_P$ 20 to the measurement magnetic field $B_M$ 22 is substantially shorter than an expected minimum longitudinal relaxation time in the region under investigation. Switching the static magnetic field intensity from $B_P$ to $B_M$ is considered an adiabatic process because the direction of the static magnetic field practically does not change. The measurement magnetic field $B_M$ 22 is applied to nuclei of the formation 4 during a measurement interval. After the switching is completed, the RF magnetic field $B_{RF}$ is applied to the nuclei in the region of investigation. The RF magnetic field $B_{RF}$ is typically pulsed in a form of CPMG pulse sequence (or CPMG pulse train). Generally, the RF magnetic field $B_{RF}$ is orthogonal to the polarizing magnetic field $B_P$ and the measurement magnetic field $B_M$. FIG. 4B illustrates an exemplary CPMG pulse sequence.

Figure 4C:
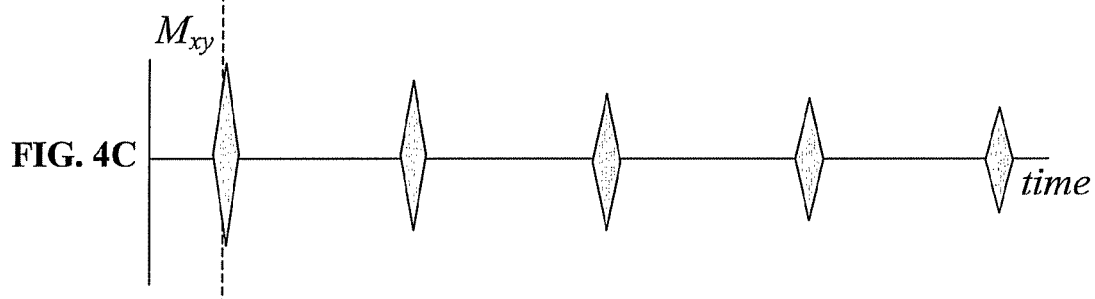
Figure 4D:

The operating frequency $\omega_0$ of the RF magnetic field $B_{RF}$ is chosen to select a desired depth of investigation $r_0$ where $r_0 \propto \sqrt{\omega_0}$. Nuclear magnetization $M_{xy}$ is in a plane perpendicular to the static magnetic field. FIG. 4C illustrates an exemplary embodiment of the nuclear magnetization $M_{xy}$. The nuclear magnetization $M_{xy}$ induces a RF spin-echo signal in an antenna in the logging instrument 10. FIG. 4D illustrates an exemplary nuclear magnetization component $M_z$. The nuclear magnetization component $M_z$ has a direction the same as the direction the polarizing magnetic field $B_P$ and the measurement magnetic field $B_M$. The direction of the polarizing magnetic field $B_P$ and the measurement magnetic field $B_M$ is the Z-axis direction where the Z-axis direction is perpendicular with the axis of the borehole 2.

Figure 5:
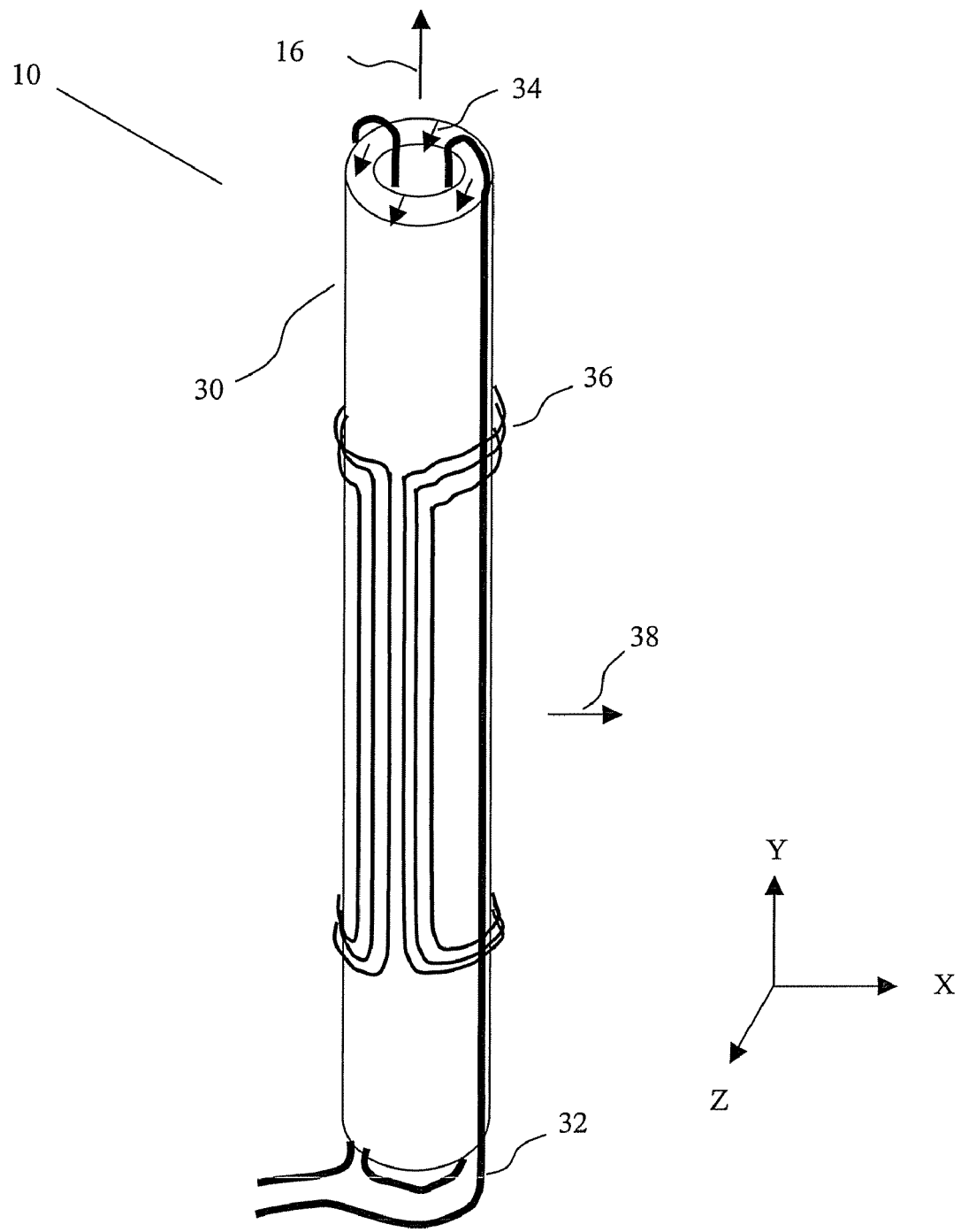
FIG. 5 illustrates an exemplary embodiment of the logging instrument for performing the NMR well logging measurements.

FIG. 5 illustrates an example of the logging instrument 10 for implementing the teachings herein. The logging instrument 10 includes a magnetic core 30 and a switching winding 32. The switching winding 32 conducts electrical current to magnetize the magnetic core 30 in direction 34 to create a transversal dipole. The transversal dipole moment is perpendicular to the axial direction 16 that is collinear to the borehole 2. The transversal dipole provides either the polarizing magnetic field $B_P$ or the measurement magnetic field $B_M$ depending on an amount of magnetization of the magnetic core 30. Referring to FIG. 5, the logging instrument 10 also includes an NMR antenna 36 for generating the RF magnetic field $B_{RF}$. A direction 38 (the X-axis direction) of the RF magnetic field $B_{RF}$ is perpendicular to the direction of the polarizing magnetic field $B_P$ and the measurement magnetic field $B_M$ (parallel to the Z-axis). The NMR antenna 36 can also be used as a receiver coil for receiving the NMR signal. As will be explained further below, it is preferable for the magnetic core 30 to have a residual magnetization after the electrical current in the switching winding 32 is removed in order to facilitate generating the polarizing magnetic field $B_P$ 20 at a high intensity.

As discussed above, the teachings are based on performing NMR measurements with (1) a high polarizing magnetic field and corresponding high nuclear magnetization in the region of investigation and (2) a relatively low measurement magnetic field $B_M$ and corresponding relatively low operating frequency $\omega_0$. The reasoning below explains how a lower measurement magnetic field $B_M$ for a given nuclear magnetization (proportional to the polarizing magnetic field $B_P$) will facilitate a high SNR.

Equation (6) for the NMR signal illustrates that, for a given nuclear magnetization $M_n$, the NMR signal does not depend on the operating frequency $\omega_0$. In order to assess what effect the low operating frequency $\omega_0$ has on the SNR, the SNR can be expressed as follows based on equation (6) and that antenna thermal noise is proportional to the square root of an effective loss resistor $R_{eff}$:

$$SNR \propto \frac{B'_{A1} \cdot n_r}{\sqrt{R_{eff}}}, \quad (7)$$

where $B'_{A1}$ is the antenna sensitivity function for the NMR antenna 36 per one turn of the antenna windings and $n_r$ is the number of turns in the receiver coil. The antenna sensitivity function depends on a geometry of a core and windings of the NMR antenna 36.

Sources contributing to the effective loss resistor $R_{eff}$ are resistance losses of wire used for the NMR antenna 36 and losses due to coupling with conductive environments. The conductive environments may include at least one of conductive drilling mud in the borehole 2 and conductive formations 4. Electric type losses $P_{lossE}$ are associated with the resistance losses and magnetic type losses $P_{lossM}$ are associated with the losses due to coupling with conductive environments. The magnetic type losses $P_{lossM}$ with a weak skin effect are proportional to magnetic flux squared and the operating frequency $\omega_0$ squared. The weak skin effect is typical for losses in the formation 4 and the borehole 2. The magnetic flux is essentially proportional to a current-turn product of the NMR antenna 36. The electric type losses $P_{lossE}$ are proportional to current squared and are linear with a number of turns in the NMR antenna 36. A frequency dependence of the electric type losses $P_{lossE}$ is approximately a square root of the frequency of current in the NMR antenna 36. Thus, total losses can be described as $$P_{loss} = P_{lossM} + P_{lossE} = (I_r \cdot n_r)^2 \cdot F_M(\omega) + I_r^2 n_r \cdot F_E(\omega) \quad (8)$$

where $I_r$ equals current in the receiver coil, $F_M(\omega) \propto \omega^2$ is the frequency dependence of the magnetic type losses $P_{lossM}$, and $F_E(\omega) \propto \sqrt{\omega}$ is the frequency dependence of the electric type losses $P_{lossE}$.

Based on the above, the effective loss resistor can be expressed as $$R_{eff} = P_{loss}/I_r^2 = k_M \cdot n_r^2 \cdot \omega^2 + k_E \cdot n_r \sqrt{\omega}, \quad (9)$$

where $k_M$ and $k_E$ are constants.

Depending on a conductivity of the conductive drilling mud and the conductive formations 4, the magnetic type losses $P_{lossM}$ can be either comparable with or dominate the electric type losses $P_{lossE}$ in a frequency range 0.5-1 MHz. The frequency range 0.5-1 MHz is typical for the logging instrument 10. If the magnetic type losses $P_{lossM}$ dominate, then it follows from equations (9) and (7) that the SNR is inversely proportional to the operating frequency $\omega_0$ and independent of the number of turns in the receiver coil such that $$SNR \propto \frac{1}{\omega_0}. \quad (10)$$

It can be seen with equations (10) and (3) that lowering the operating frequency $\omega_0$ and, correspondingly, lowering the measurement magnetic field $B_M$ results in a higher SNR. The higher SNR is based on the nuclear polarization provided by the polarizing magnetic field $B_P$ not being reduced when the operating frequency $\omega_0$ is reduced.

The operating frequency $\omega_0$ may be reduced to a point where the magnetic type losses $P_{lossM}$ become negligible with respect to the electric type losses $P_{lossE}$ in equation (9). When the magnetic type losses $P_{lossM}$ are negligible with respect to the electric type losses $P_{lossE}$, then the SNR can be expressed as $$SNR \propto \sqrt{n_r} \cdot \sqrt[4]{\frac{1}{\omega_0}}. \quad (11)$$

Thus, when a low operating frequency regime characterized by negligible magnetic type losses $P_{lossM}$ is reached, a further increase in the SNR becomes possible by increasing the number of turns in the receiver coil. With respect to equation (11), the SNR has a weak operating frequency $\omega_0$ dependence.

A higher limit for the number of turns in the receiver coil is normally set by stray capacitance and corresponding self-resonances in the receiver coil. A lower operating frequency $\omega_0$ will provide for an increased number of turns in the receiver coil.

In accordance with the Reciprocity Principle, an increased number of turns in the NMR antenna 36 is beneficial to generating the RF magnetic field. Expressions for power loss related to the NMR antenna 36 can be developed as:

$$P_{loss} = P_{lossM} + P_{lossE} = (I \cdot n_s)^2 \cdot F_M(\omega) + I^2 n_s \cdot F_E(\omega) \quad (12)$$

where $n_s$ is the number of turns in the NMR antenna 36. Electrical current in the NMR antenna 36 required for a given RF magnetic field intensity $B_{RF}$ is inversely proportional to the number of turns $n_s$. The electrical current can be expressed as $I \propto 1/n_s$. Thus, for a low operating frequency $\omega_0$, the magnetic type losses $P_{lossM}$ in equation (12) can be neglected and equation (12) can be rewritten as:

$$P_{loss} \propto \frac{1}{n_s} \cdot \sqrt{\omega_0}. \quad (13)$$

By determining the power loss $P_{loss}$ related to the NMR antenna 36 and the electrical current I, the effective loss resistor of the NMR antenna 36 can be determined using equation (9).

Equations (13) and (11) can be combined to obtain the following expression for NMR sensor efficiency:

$$\frac{SNR}{\sqrt{P_{loss}}} \propto \frac{\sqrt{n_r \cdot n_s}}{\sqrt{\omega_0}}. \quad (14)$$

A higher number of turns in the NMR antenna 36 typically does not require a substantial increase in cross-sectional area of windings of the NMR antenna 36. Less skin and proximity effects at the lower operating frequency $\omega_0$ provide for better utilization of the cross-sectional area of the windings.

Figure 6:
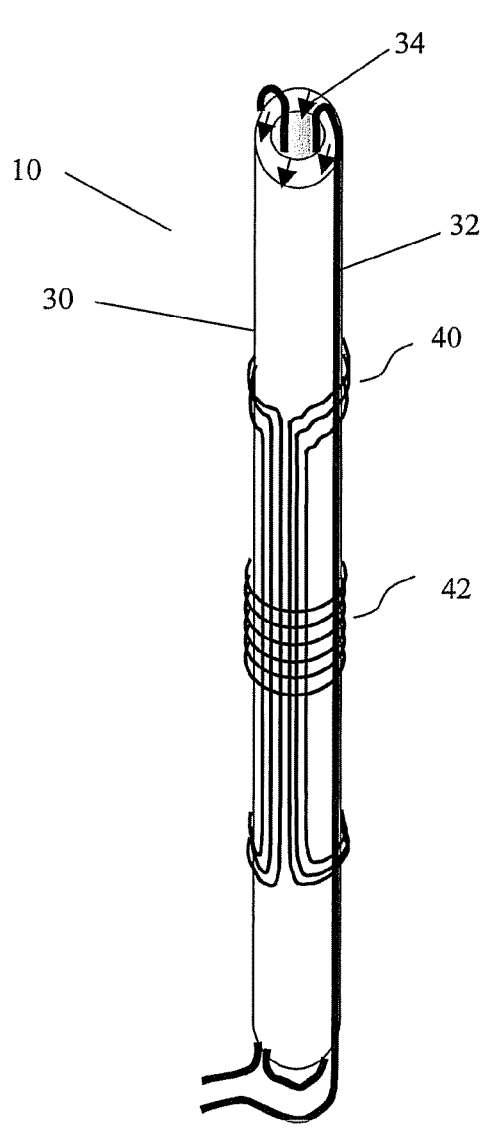
FIG. 6 illustrates an exemplary embodiment of the logging instrument with two antennas.
Figure 7:
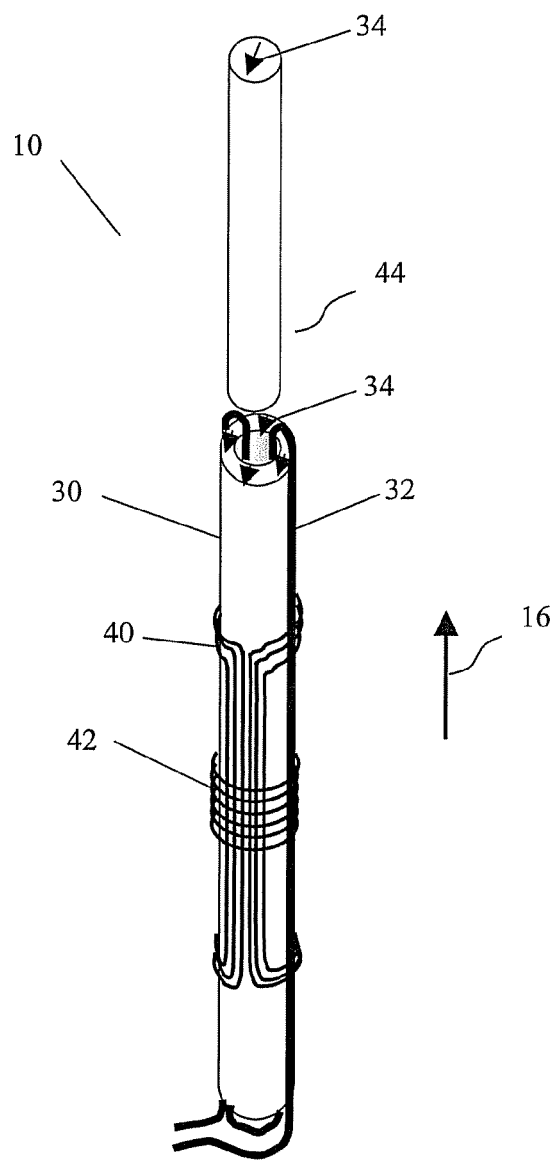
FIG. 7 illustrates an exemplary embodiment of the magnet assembly with two antenna and a pre-polarizing permanent magnet.

One advantage of the high SNR is that NMR logging speed can be increased. However, the logging instrument 10 must be designed for increased NMR logging speed. A desired NMR logging speed is about thirty to forty feet per minute with a vertical resolution of measurements of about two to four feet. A practical limit of the NMR logging speed is normally placed by a number of measurement cycles needed for stacking data and achieving adequate SNR. For example, for an aperture two feet long in the NMR antenna 36, an NMR logging speed of forty feet per minute, and a measurement cycle interval (CPMG train length) of 1.5 seconds, the displacement of the logging instrument 10 is one foot. Noticeable signal decay can be expected due to improper RF excitation conditions. The improper RF excitation conditions result because a significant part of the region of investigation exposed to the frequently coming CPMG pulses is not affected by the ninety-degree preparatory pulse. One solution is to use the NMR antenna 36 that has an aperture that is substantially longer than the displacement of the logging instrument 10 during one measurement cycle interval. However, the substantially longer aperture will provide poorer vertical resolution of measurements. Another solution is to use two antennas of different lengths. FIG. 6 illustrates an exemplary embodiment of the logging instrument 10 with two antennas. Referring to FIG. 6, the logging instrument 10 includes a long antenna 40 and a short antenna 42. The long antenna 40 transmits RF pulses (also referred to as the CPMG pulses or refocusing pulses) over a sufficient length in a direction of motion of the logging instrument 10. The direction of motion is depicted as the axial direction 16 in FIG. 6. The short antenna 42 receives the NMR signals induced by precession of the nuclei in the region of investigation. Typically, the short antenna 42 does not move beyond a region that is affected by the preparatory pulse and the refocusing pulses. In order to speed up recovery of high nuclear polarization that is associated with the polarizing magnetic field $B_P$, a pre-polarizing permanent magnet can be placed ahead of the magnetic core 30. FIG. 7 illustrates an exemplary embodiment of the logging instrument 10 (moving in the axial direction 16) with two antennas and a pre-polarizing permanent magnet 44.

FIG. 8 illustrates exemplary aspects of a fast switchable source for producing the polarizing magnetic field $B_P$ and the measurement magnetic field $B_M$. Referring to FIG. 8A, a first winding 52 and a second winding 54 are shown disposed on opposite sides of the of the magnetic core 30. In some embodiments, the first winding 52 and the second winding 54 may be one continuous winding such as the switching winding 32 shown in FIG. 5. For fast switching, the first winding 52 and the second winding 54 require low inductance. In general, the low inductance is achieved by using a small number of turns, in some cases only one turn in each of the first winding 52 and the second winding 54. During operation of the fast switchable source, a pulse of current is applied to each of the first winding 52 and the second winding 54 in a direction 56 as depicted in FIG. 8A. The pulse of current creates magnetization of the magnetic core 30 in substantially a transversal direction. The magnetization in the transversal direction creates a transversal magnetic dipole. FIG. 8B illustrates a top cross-sectional view of the magnetic core 30 depicting transversal magnetization 58.

Figure 8A:
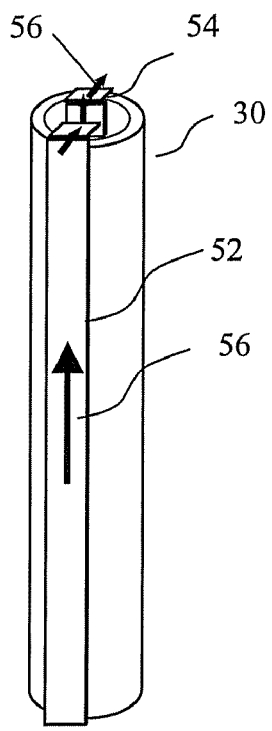
FIGS. 8A, 8B, 8C, and 8D, collectively referred to as FIG. 8, illustrate exemplary aspects of a fast switchable source of a polarizing magnetic field.
Figure 8C:
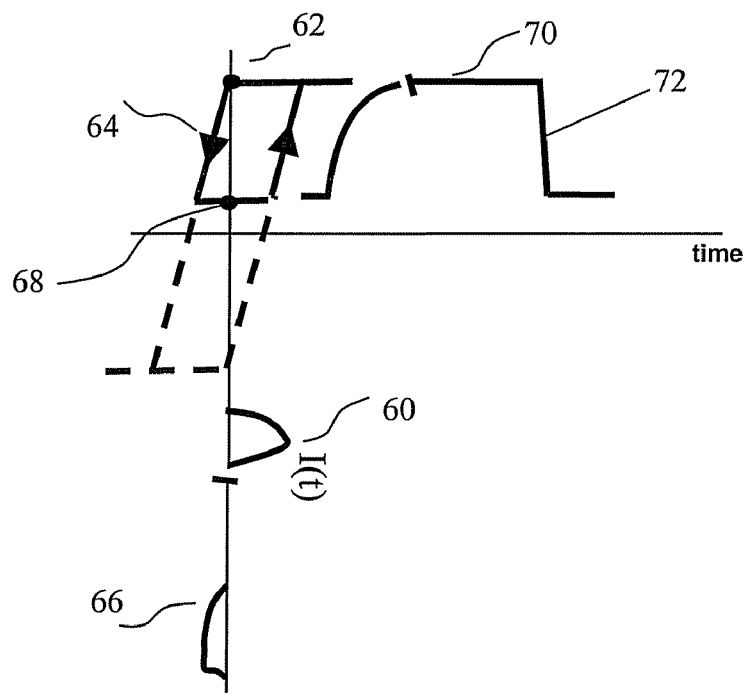
Figure 8B:
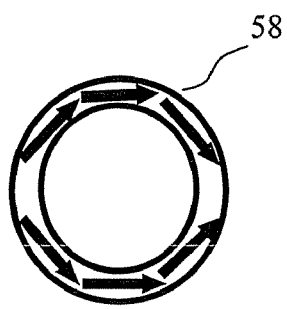
Figure 8D:
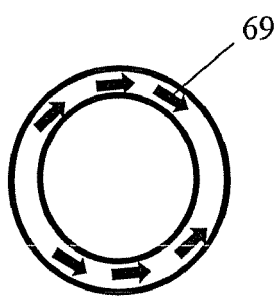

The magnetic core 30 is made from a magnetic material that has substantial hysteresis. The hysteresis results in residual magnetization remaining after the pulse of current. FIG. 8C illustrates an exemplary hysteresis cycle 64 corresponding to switching the transverse magnetic dipole "on" and "off." Referring to FIG. 8C, after a first current pulse 60, magnetization of the magnetic core 30 corresponds to residual magnetization 62. Typically, strength of the transversal magnetization 58 corresponds to the residual magnetization 62. At the residual magnetization 62, no electrical current is required in the first winding 52 and the second winding 54 to maintain the magnetization in the magnetic core 30. Correspondingly, no electrical current is required in the first winding 52 and the second winding 54 to maintain a magnetic field in the region of investigation in the formation 4. The residual magnetization 62 makes the fast switchable source effective enabling 2,500 A·m² magnetic dipole per 1 m length to be generated with DC power consumption of about 200 W for four seconds of a magnetization-demagnetization cycle. Again referring to FIG. 8C, a second current pulse 66 demagnetizes the magnetic core 30 to a low magnetization state 68 corresponding to the measurement magnetic field $B_M$. FIG. 8C also illustrates a time dependent magnetic field 70 that includes the polarizing magnetic field $B_P$ and the measurement magnetic field $B_M$. The magnetic field 70 includes a trailing edge 72. A time interval corresponding to the trailing edge 72 is short enough to ensure that no significant longitudinal relaxation occurs during the time interval but also long enough for switching intensities of the magnetic field 70 from $B_P$ to $B_M$ to be the adiabatic process discussed above. FIG. 8D illustrates a top cross-sectional view of the magnetic core 30 depicting reduced transversal magnetization 69. Typically, the reduced transversal magnetization 69 corresponds to the low magnetization state 68 on the hysteresis cycle 64.

Another embodiment of the fast switchable source can be based on a longitudinal magnetic dipole. The longitudinal magnetic dipole is developed from magnetization of the magnetic core 30 directed along the longitudinal axis of the magnetic core 30. A switching winding for creating the longitudinal magnetic dipole can be a solenoid-type coil disposed about the magnetic core 30 similar to the short antenna 42 depicted in FIG. 6.

Figure 9:
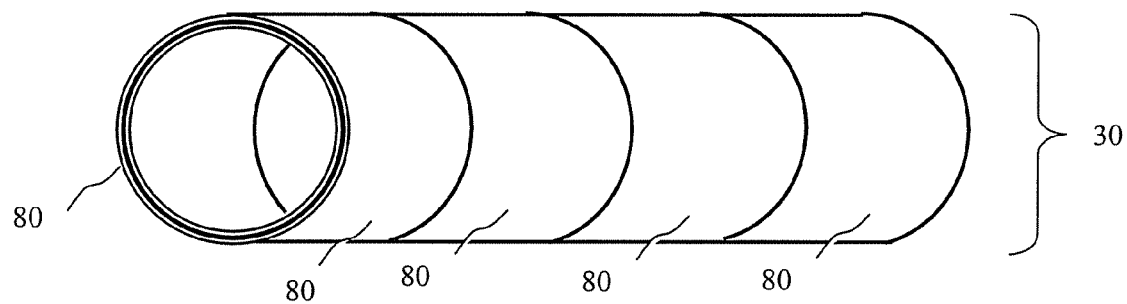
FIG. 9 illustrates an exemplary embodiment of a magnetic core made with a stack of ribbon wound rings.

FIG. 9 illustrates an exemplary embodiment of the magnetic core 30. Referring to FIG. 9, the magnetic core 30 is made of a stack of ribbon wound rings 80. The ribbon wound rings 80 can be made from an amorphous magnetic material.

Figure 10:
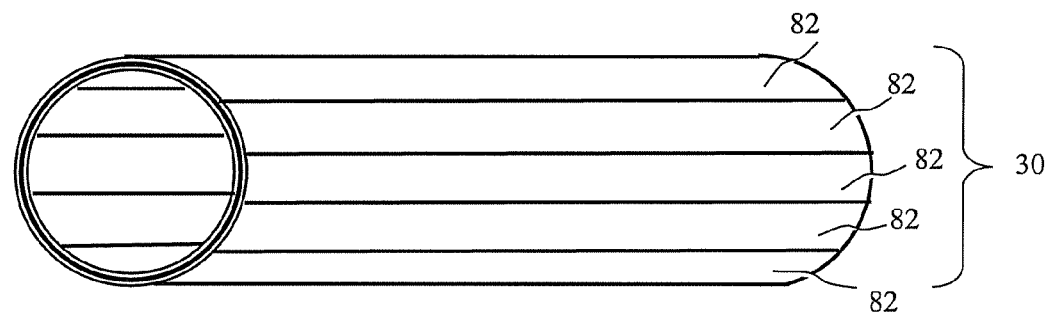
FIG. 10 illustrates an exemplary embodiment of the magnetic core made with longitudinal packs.

FIG. 10 illustrates another exemplary embodiment of the magnetic core 30. Referring to FIG. 10, the magnetic core 30 is made from longitudinal packs 82. The longitudinal packs 82 can be made of amorphous magnetic ribbons that are suitable for longitudinal magnetization.

The ribbons in the packs 82 or the rings 80 are separated with non-conducting layers. The ribbon thickness is chosen to be thin enough to reduce eddy current in the electrically conductive ribbons. The eddy current could otherwise cause undesired delay in switching the static magnetic field between $B_P$ and $B_M$.

The magnetic core 30 can also be made of a non-conductive ferrite-type magnetic material.

Figure 11A:
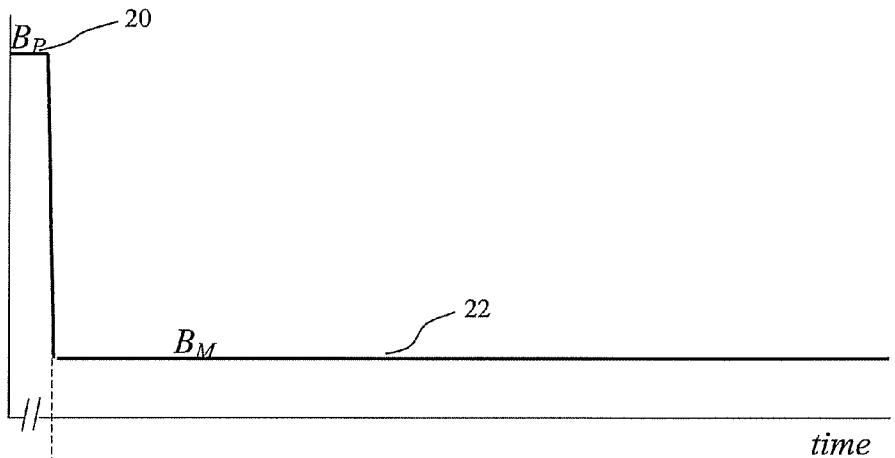
FIGS. 11A, 11B, 11C, and 11D, collectively referred to as FIG. 11, illustrate exemplary graphs of a static magnetic field with one intensity, two CPMG trains, and magnetization versus time.
Figure 11B:
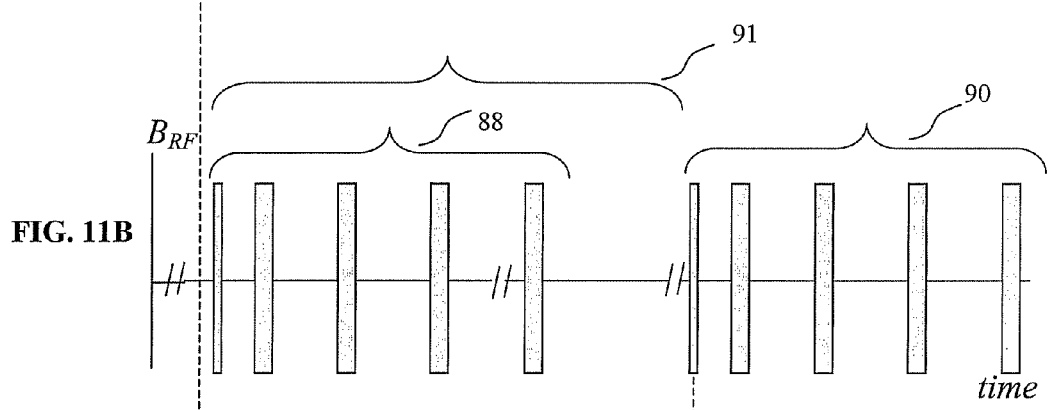
Figure 11C:
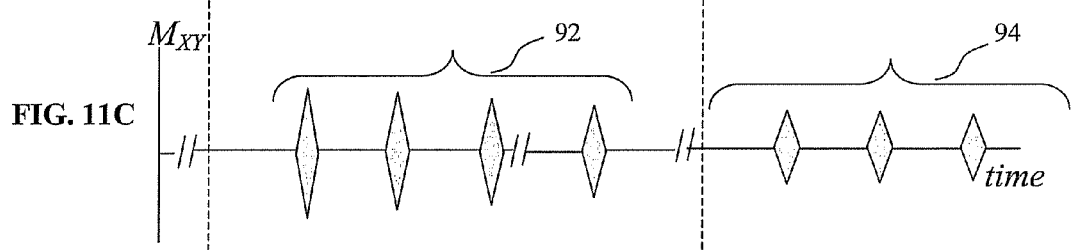
Figure 11D:
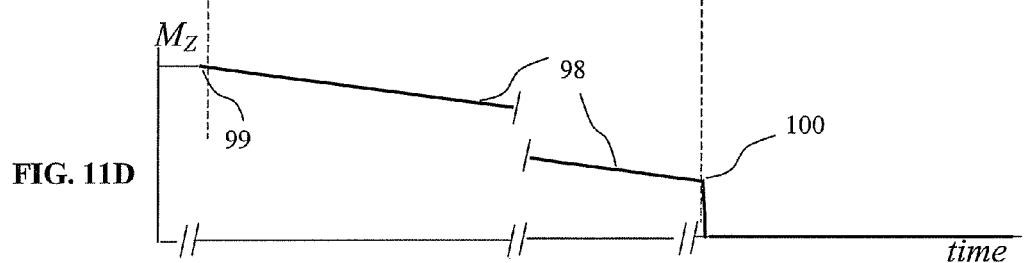

FIG. 11 illustrates an example of graphs of magnetic fields and magnetizations associated with the logging instrument 10 performing NMR measurements. Referring to FIG. 11A, the polarizing magnetic field $B_P$ 20 is switched to the measurement magnetic field $B_M$ 22. After the switching has occurred, at least two CPMG pulse trains are run consecutively. For teaching purposes, only two CPMG pulse trains are discussed, a first CPMG train 88 and a second CPMG train 90 as depicted in FIG. 11B. The first CPMG train 88 has an operating frequency $\omega_{01}$ slightly different from the operating frequency $\omega_{02}$ of the second CPMG train 90. Separation between the operating frequencies $\omega_{01}$ and $\omega_{02}$ is large enough to spatially separate excitation regions in accordance with $r_0 \propto \sqrt{\omega_0}$. However, the excitation regions are spatially close enough to attribute the NMR signals to approximately the same depth of investigation. When the first CPMG train 88 is run, excitation conditions are achieved at the excitation region near $r_{01}$ (referred to as the first region) with thickness $$\Delta r = \frac{\Delta \omega}{\gamma \cdot G_{01}}$$

where $G_{01}$ is the gradient of the measurement magnetic field $B_M$ at $r_{01}$. After the preparatory pulse of the first CPMG train 88, magnetization of the first region is substantially in a plain perpendicular to the direction of the measurement magnetic field $B_M$. The magnetization beyond the first region in a region referred to as the second region is substantially not affected by the first CPMG train 88. The magnetization of the second region decays to a new equilibrium state corresponding to the measurement magnetic field $B_M$. FIG. 11D illustrates an example of a longitudinal component of nuclear magnetization in the second region. The longitudinal component is generally in the Z-axis direction perpendicular to the axial direction 16 (see FIG. 5). Referring to FIG. 11D, the longitudinal component decays along curve 98 from initial polarizing magnetization $M_{ZP}$ 99 to initial magnetization condition $M_{Z2}$ 100. The second CPMG train 90 is run after a time interval 91 (see FIG. 11B) having a duration of TR. The second CPMG train 90 excites nuclei in the second region. FIG. 11C illustrates examples of the spin-echo signals resulting from the CPMG pulse trains. Referring to FIG. 11C, a first echo train 92 results from the first CPMG train 88 and a second echo train 94 results from the second CPMG train 90. The first echo train 92 and the second echo train 94 are also referred to as a transversal component of nuclear magnetization. The transversal component of nuclear magnetization is typically in the X-Y plane.

The longitudinal component of nuclear magnetization as a function of time (i.e., the curve 98) can be expressed as:

$$M_{Z2}(TR) = (M_{ZP} - M_{Z0}) \cdot e^{\frac{TR}{T_1}} + M_{Z0}. \tag{15}$$

In equation (15), $M_{ZP}$ is the initial polarizing magnetization 99 for the first CPMG train 88 at the operating frequency $\omega_{01}$; $M_{Z2}$ (TR) is the initial magnetization condition 100 for the second CPMG train 90 at the operating frequency $\omega_{02}$ as a function of TR; $T_1$ is the longitudinal relaxation time. The initial polarizing magnetization 99 is acquired through measurement of an amplitude of the first echo train 92. Similarly, the initial magnetization condition 100 is acquired through measurement of an amplitude of the second echo train 94.

Based on equation (15), the $T_1$ relaxation time can be assessed. A plurality of operating frequencies can be used to acquire a set of points on a $T_1$ relaxation curve. Simultaneously, $T_2$ relaxation data is obtained from a plurality of the CPMG echo trains.

An estimate may be made of the longitudinal relaxation time to reduce the duration of the polarizing magnetic field. In cases of multi-exponential relaxation spectrum, the estimate will use the longest component. The estimate males it possible to extrapolate and therefore correct to a full polarization in situations when complete nuclear polarization does not occur.

FIG. 12 illustrates another example of graphs of magnetic fields and magnetizations associated with the logging instrument 10 performing NMR measurements. FIG. 12A illustrates the polarizing magnetic field $B_P$ 20 and an exemplary measurement magnetic field with two intensities $B_{M1}$ and $B_{M2}$. A first measurement magnetic field $B_{M1}$ 102 and a second measurement magnetic field $B_{M2}$ 104 are shown in FIG. 12A. The two intensities $B_{M1}$ and $B_{M2}$ provide for selecting the first region and the second region rather then using the two CPMG pulse trains with different operating frequencies as depicted in FIG. 11B. The first CPMG train 88 and the second CPMG train 90 depicted in FIG. 12B have the same operating frequency $\omega_0$. FIG. 12C illustrates an example of a graph of the transversal component of nuclear magnetization versus time for the echo-spin signals resulting from the first CPMG train 88 and the second CPMG train 90. FIG. 12D illustrates an example of a graph of the longitudinal component of nuclear magnetization versus time.

The operation of the logging instrument 10 as depicted in FIGS. 4, 11, and 12 does not specify any experiments or measurements to be conducted during a polarization interval. The polarization interval is a time interval during which the polarizing magnetic field $B_P$ 20 is applied to the formation 4. It is preferable that the polarization interval be used to acquire additional information. The polarization interval can be used to acquire NMR relaxation data from a region substantially deeper than the first region and the second region.

Figure 13A:
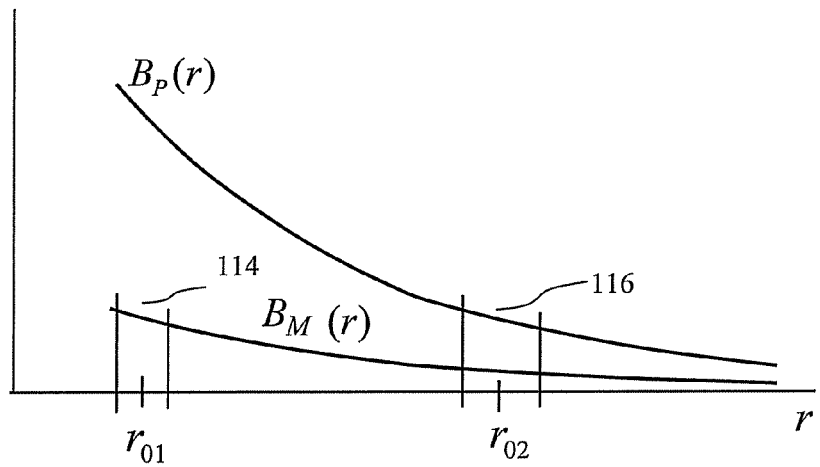
FIGS. 13A, 13B, and 13C, collectively referred to as FIG. 13, illustrate exemplary aspects of acquiring NMR relaxation data from a substantially deeper region.
Figure 13B:
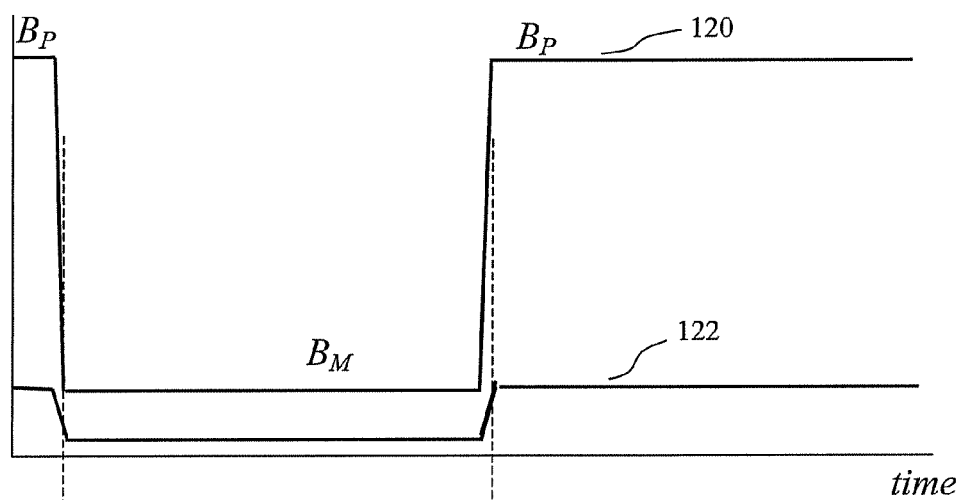
Figure 13C:
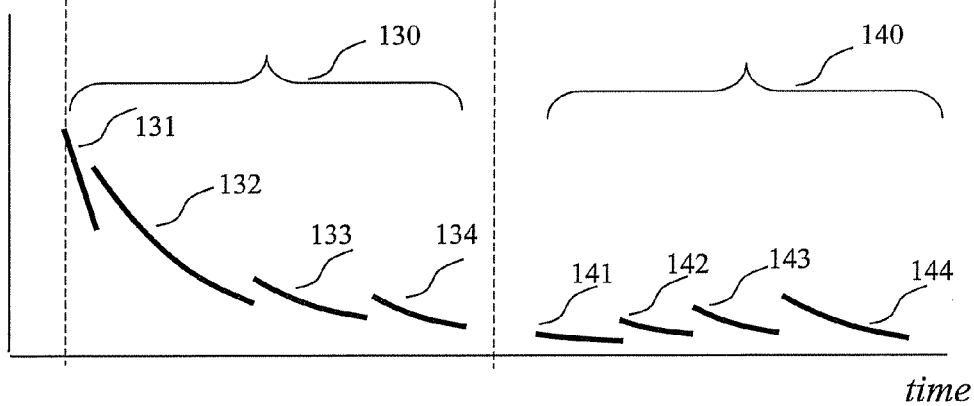

FIG. 13 depicts exemplary aspects of the operation of the logging instrument 10 to acquire the NMR relaxation data from substantially deeper regions of the formation 4. FIG. 13A illustrates exemplary aspects of radial dependence of the polarizing magnetic field $B_P$ 20 as a function of radius r and the measurement magnetic field $B_M$ 22 as a function of r. Referring to FIG. 13A, a first excitation region 114 about $r_{01}$ is excited by the measurement magnetic field $B_M$ 22 and the CPMG pulse train with the operating frequency $\omega_0$. A second excitation region 116 about $r_{02}$ is excited by the polarizing magnetic field $B_P$ 20 and the CPMG pulse train with the operating frequency $\omega_0$. FIG. 13 B illustrates an exemplary cycling diagram for the static magnetic field. Referring to FIG. 13B, aspects of cycling a first static magnetic field 120 and a second static magnetic field 122 are illustrated. The first static magnetic field 120 corresponds to the first excitation region 114. Similarly, the second static magnetic field 122 corresponds to the second excitation region 116. For the operation of the logging instrument 10 depicted in FIG. 13, two groups of CPMG pulse trains are employed. Referring to FIG. 13C, a first CPMG pulse train group represented by echo train curves 131-134 is applied during a first interval 130. The first interval 130 occurs during application of the measurement magnetic field $B_M$ 22. The first CPMG pulse train group typically includes a plurality of CPMG pulse trains similar to the first CPMG train 88 and the second CPMG train 90 in FIG. 11B or 12B.

First echo train curves 131-134 are derived from points corresponding to spin-echo magnitudes such as the spin-echo magnitudes depicted in FIG. 4C for a single CPMG echo train. Again referring to FIG. 13C, a second CPMG pulse train group is applied during a second time interval 140. The second CPMG pulse train group is applied during application of the polarizing magnetic field $B_P$ to the second excitation region 116. The second time interval 140 includes second echo train curves 141-144. As the nuclear magnetization in the second excitation region 116 increases (due to the static magnetic field increasing in intensity from $B_M$ to $B_P$), starting points of each echo train curve (i.e., starting spin-echo magnitudes) increase according to the $T_1$ relaxation curve. As with the operations depicted in FIG. 11, each of the CPMG pulse trains related to the first echo train curves 131-134 are run at slightly different frequencies in order to spatially separate the excitation regions. The second CPMG pulse train group related to the second echo train curves 141-144 may have the same set of operating frequencies as the first CPMG pulse train group related to the first echo train curves 131-134. Spatial separation of the excitation regions resulting from the first CPMG pulse train group and the second CPMG pulse train group is ensured by radial dependence of the polarizing magnetic field $B_P$ and the measurement magnetic field $B_M$. Choosing the same set of operating frequencies for the first time interval 130 and the second time interval 140 means that the measurement magnetic field $B_M$ corresponding to radius of investigation $r_{o1}$ is equal to the polarizing magnetic field $B_P$ corresponding to the radius of investigation $r_{o2}$ (see curves $B_P(r)$ and $B_M(r)$ in FIG. 13A).

A comparison between the first echo train curves 131-134 and the second echo train curves 141-144 provides valuable information on radial dependence of properties of the formation 4 related to invasion of a bore mud filtrate. In general, an invasion profile of the bore mud filtrate is indicative of the permeability of the formation 4.

Figure 14:
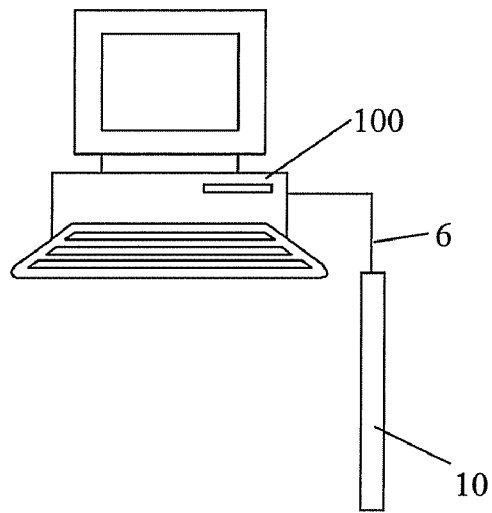
FIG. 14 illustrates an exemplary embodiment of a computer coupled to the logging instrument.

Referring to FIG. 14, an apparatus for implementing the teachings herein is depicted. In FIG. 14, the apparatus includes a computer 100 coupled to the well logging instrument 10. Typically, the computer 100 includes components as necessary to provide for operating the well logging instrument 10. Exemplary components include, without limitation, at least one processor, storage, memory, input devices, output devices and the like. As these components are known to those skilled in the art, these are neither depicted in any detail nor discussed further herein.

Typically, the teachings herein are reduced to an algorithm that is stored on machine-readable media. The algorithm is implemented by the computer 100 and provides for measuring properties of the formation 4 from the borehole 2.

Figure 15:
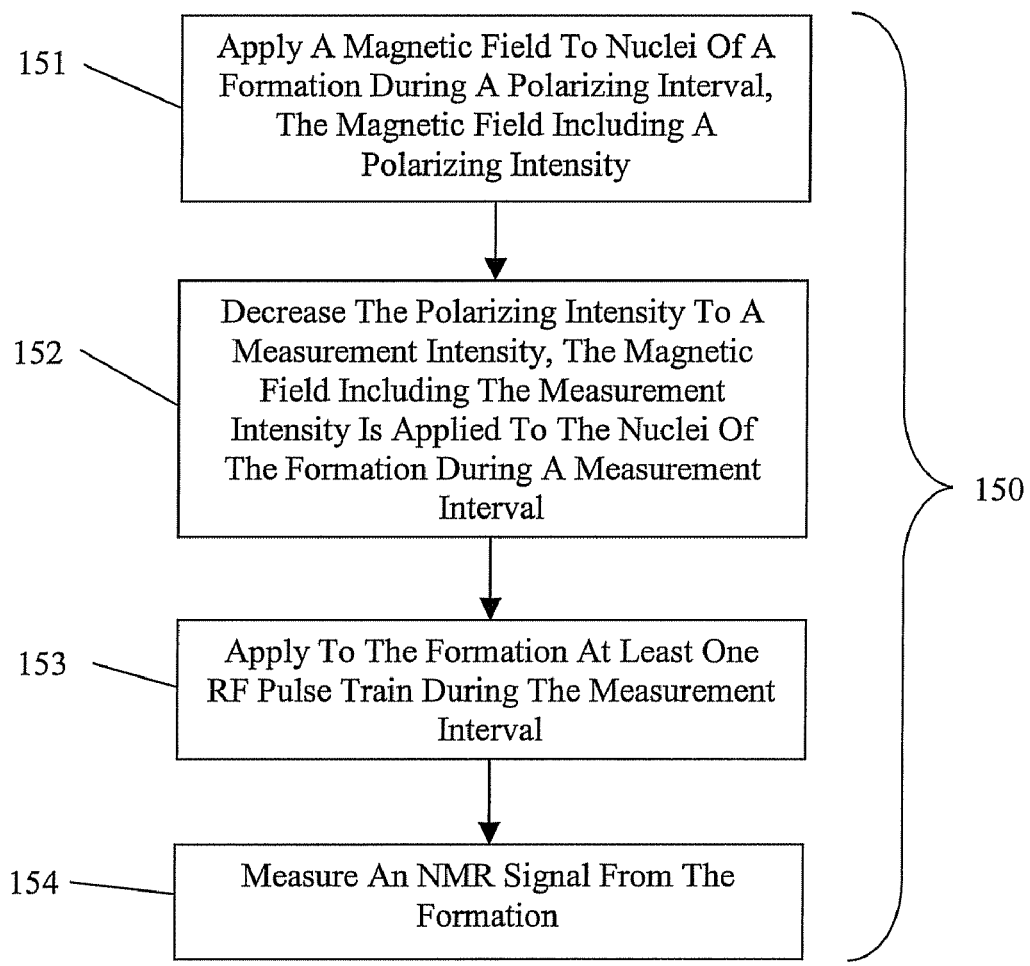
FIG. 15 presents an exemplary method for operating the logging instrument to perform NMR measurements in the borehole.

FIG. 15 presents an exemplary method 150 for operating the logging instrument 10 to perform NMR measurements in the borehole 2. A first step 151 calls for applying a magnetic field with a polarizing intensity to polarize nuclei of the formation 4 during the polarization interval. A second step 152 calls for decreasing the intensity of the magnetic field to a measurement intensity. The magnetic field with the measurement intensity is applied to the nuclei of the formation 4 during the measurement interval. A third step 153 calls for applying to the formation 4 at least one RF pulse train. A fourth step 154 calls for measuring an NMR signal from the formation 4.

Figure 16:
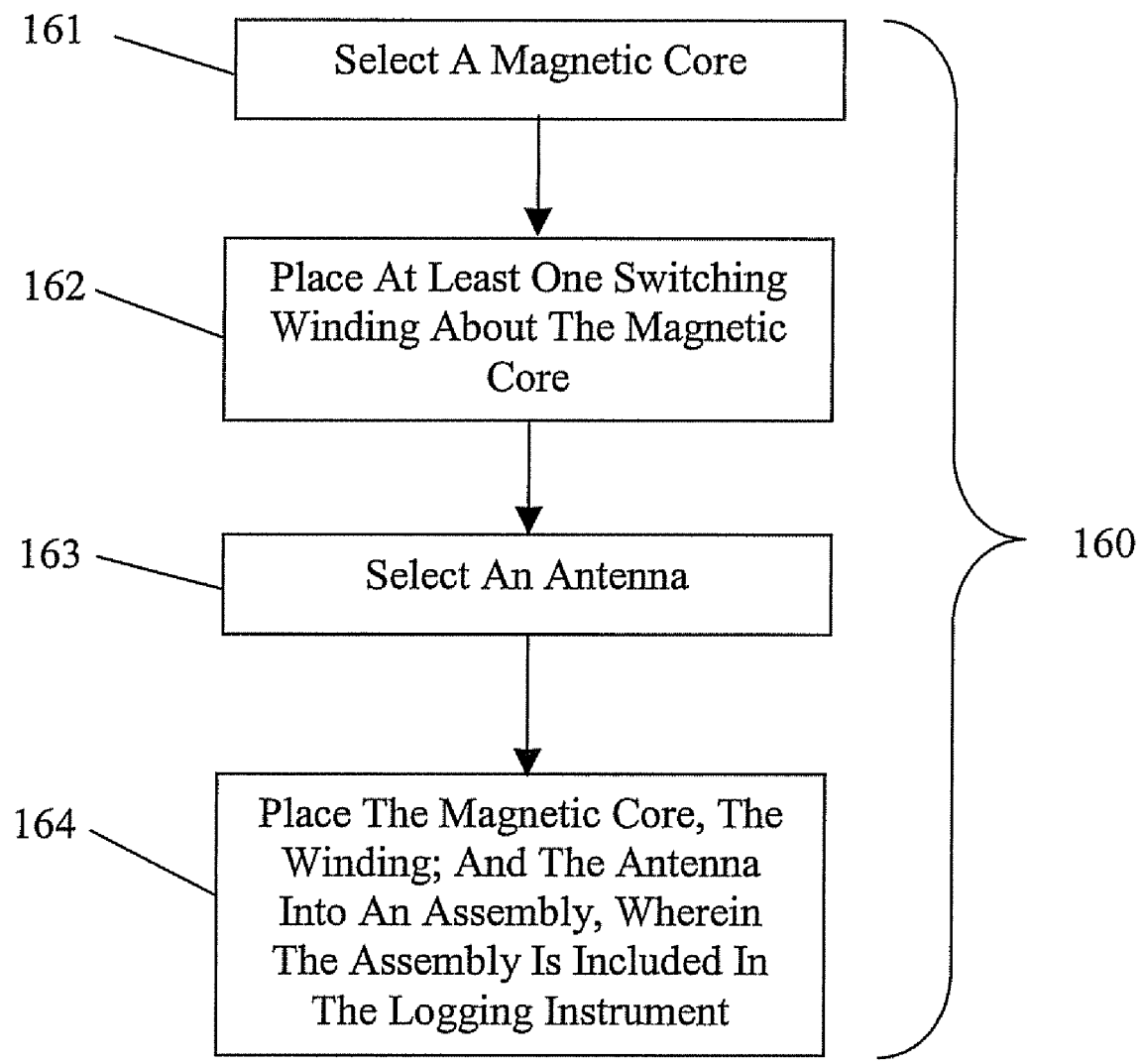
FIG. 16 presents an exemplary method for producing the logging instrument.

FIG. 16 presents an exemplary method 160 for producing the logging instrument 10. A first step 161 calls for selecting a magnetic core 30. A second step 162 calls for placing at least one switching winding 32 about the magnetic core 30. Typically, the switching winding 32 conducts electrical current to magnetize the magnetic core 30 and is adapted to switch between the polarizing magnetic field $B_P$ 20 and the measurement magnetic field $B_M$ 22. A third step 163 calls for selecting an antenna 36. A fourth step 164 calls for placing the magnetic core 30, the switching winding 32, and the antenna 36 into an assembly, wherein the assembly is included in the logging instrument.

In support of the teachings herein, various analysis components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, power supply (e.g., at least one of a generator, a remote supply and a battery), pressure supply, cooling unit, motive force (such as a translational force, propulsional force or a rotational force), magnet, electromagnet, transceiver, controller, optical unit, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for measuring nuclear magnetic resonance (NMR) relaxation properties of a formation with a high signal to noise ratio (SNR), the method comprising:
    applying a magnetic field to nuclei of the formation during a polarizing interval, the magnetic field comprising a polarizing intensity having a constant magnitude resulting in a longitudinal magnetization ($M_z$) of the nuclei wherein the polarizing interval begins and ends before the ($M_z$) decreases;
    decreasing the applied magnetic field to a measurement intensity having a constant magnitude, the measurement intensity magnetic field applied to the nuclei of the formation during a measurement interval wherein a time interval for the decreasing is substantially shorter than a minimum longitudinal relaxation time of the nuclei;
    applying to the formation at least one radio frequency (RF) pulse train during the measurement interval;
    measuring an NMR signal from the formation in order to measure the NMR relaxation properties with the high SNR; and
    using a processor in order to perform at least one of the following tasks: store the NMR signal, analyze the NMR signal, use the NMR signal for equipment operation, and present the NMR signal to a user.

2. The method of claim 1, wherein the NMR relaxation properties of the formation are measured outside of/beyond a region invaded by a drilling mud spurt.

3. The method as in claim 1, wherein the at least one RF pulse train comprises a CPMG pulse train and wherein the NMR signals comprise information regarding a transverse relaxation time, $T_2$, for the nuclei.

4. The method as in claim 1, wherein the NMR signals comprise information regarding a longitudinal relaxation time, $T_1$, for the nuclei.

5. The method as in claim 1, further comprising changing the magnetic field during the measurement interval to at least one additional measurement intensity in order to acquire information on a longitudinal relaxation time, $T_1$, for the nuclei.

6. The method as in claim 1, further comprising at least one additional RF pulse train applied during the measurement interval, wherein the RF pulse trains comprise slightly different operating frequencies.

7. The method as in claim 1, further comprising at least one RF pulse train applied to the formation during the polarizing interval.

8. The method as in claim 7, further comprising at least one additional RF pulse train applied during the polarization interval, the at least one additional RF pulse train comprising an operating frequency slightly different from the at least one RF pulse train applied during the polarization interval.

9. The method as in claim 7, further comprising changing the intensity of the magnetic field applied during the polarizing interval to at least one additional polarizing intensity during the polarizing interval.

10. An instrument configured for measuring nuclear magnetic resonance (NMR) relaxation properties of a formation with a high signal to noise ratio (SNR) from a borehole, the instrument comprising:
    a magnetic core;
    at least one switching winding disposed about the magnetic core, wherein the winding conducts electrical current to magnetize the core and is configured to switch from a polarizing magnetic field comprising a polarizing intensity having a constant magnitude to a measurement magnetic field comprising a measurement intensity having a constant magnitude that is less than the polarizing intensity during a time interval that is substantially shorter than a minimum longitudinal relaxation time of nuclei in the formation wherein the instrument is configured to apply the polarizing magnetic field during a polarizing interval resulting in a longitudinal magnetization ($M_z$) of the nuclei wherein the polarizing interval begins and ends before the ($M_z$) decreases and wherein the instrument is further configured to apply the magnetic field with the measurement intensity during a measurement interval; and
    an antenna for at least one of transmitting a radio frequency (RF) pulse train during the measurement interval and receiving an NMR signal configured for measuring the NMR relaxation properties with the high SNR.

11. The instrument as in claim 10, wherein the winding is disposed about the magnetic core to form at least one of a transversal magnetic dipole and a longitudinal magnetic dipole.

12. The instrument as in claim 10, wherein the magnetic core comprises a magnetic material, the magnetic material comprising a substantial magnetic hysteresis, wherein the hysteresis provides for residual magnetization of the core after electrical current ceases in the winding.

13. The instrument as in claim 11, wherein the magnetic core comprises a series of ribbon wound rings connected longitudinally, the rings comprising amorphous magnetic material.

14. The instrument as in claim 11, wherein the magnetic core comprises a series of longitudinal slats, the slats comprising at least one strip of ribbon, the ribbon comprising an amorphous magnetic material.

15. The instrument as in claim 10, further comprising at least one other antenna for at least one of transmitting the RF pulse train and receiving the NMR signal.

16. The instrument as in claim 10, further comprising a magnet preceding the magnetic core in a direction of travel along a borehole axis.

17. The instrument as in claim 12, wherein the magnetic core comprises a non-conductive ferrite magnetic material.

18. A computer readable medium, the medium comprising computer readable instructions which when executed by a computer measure nuclear magnetic resonance (NMR) relaxation properties of a formation with a high signal to noise ratio (SNR), by implementing a method comprising:
    applying a magnetic field to nuclei of the formation during a polarizing interval, the magnetic field comprising a polarizing intensity having a constant magnitude resulting in a longitudinal magnetization ($M_z$) of the nuclei wherein the polarizing interval begins and ends before the ($M_z$) decreases;
    decreasing the magnetic field to a measurement intensity having a constant magnitude, the measurement intensity magnetic field applied to the nuclei of the formation during a measurement interval wherein a time interval for the decreasing is substantially shorter than a minimum longitudinal relaxation time of the nuclei;
    applying to the formation at least one radio frequency (RF) pulse train during the measurement interval;

measuring an NMR signal from the formation in order to measure the NMR relaxation properties with the high SNR; and performing at least one of the functions of storing the NMR signal on a storage medium and providing the NMR signal to a user via a user interface.

19. A method for producing a logging instrument configured for measuring nuclear magnetic resonance (NMR) relaxation properties of a formation from a borehole with a high signal to noise ratio (SNR), the method comprising:

selecting a magnetic core;

placing at least one switching winding about the magnetic core, wherein the winding conducts electrical current in order to magnetize the core and is configured to switch from a polarizing magnetic field comprising a polarizing intensity having a constant magnitude to a measurement magnetic field comprising a measurement intensity having a constant magnitude that is less than the polarizing intensity during a time interval that is substantially shorter than a minimum longitudinal relaxation time of nuclei in the formation wherein the instrument is configured to apply the polarizing magnetic field during a polarizing interval resulting in a longitudinal magnetization ($M_z$) of the nuclei;

wherein the polarizing interval begins and ends before the ($M_z$) decreases; and wherein the instrument is further configured to apply the magnetic field with the measurement intensity during a measurement interval;

selecting an antenna configured to perform the function of at least one of a) transmitting a radio frequency (RF) pulse train during the measurement interval;

b) receiving an NMR signal, which measures the NMR relaxation properties with the high SNR; and placing the magnetic core, the at least one switching winding, and the selected antenna into an assembly, wherein the logging instrument comprises the assembly into which the magnetic core, the at least one switching winding, and the selected antenna are placed.

* * * * *